(12) United States Patent
Houdebine et al.

(10) Patent No.: US 6,268,545 B1
(45) Date of Patent: *Jul. 31, 2001

(54) TRANSGENIC NON-HUMAN MAMMAL COMPRISING A RABBIT WAP PROMOTER, USES THEREOF, AND A DNA CONSTRUCT COMPRISING THE RABBIT WAP PROMOTER

(75) Inventors: Louis-Marie Houdebine, Buc; Eve Devinoy, Gif-sur-Yvette; Dominique Thepot, Livry-Gargan, all of (FR)

(73) Assignee: Institut National de la Recherche Agronomique, Paris Cedex (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/314,127

(22) Filed: May 19, 1999

Related U.S. Application Data

(63) Continuation of application No. 08/162,146, filed on Feb. 10, 1994.

(30) Foreign Application Priority Data

Jun. 12, 1991 (FR) .................................................. 91 07179

(51) Int. Cl.$^7$ .......................... A01K 67/027; C12P 21/00; C12N 5/00; C07H 21/04
(52) U.S. Cl. ................................. 800/14; 800/7; 435/325; 435/320.1; 536/24.1
(58) Field of Search ................................... 800/7, 14, 15, 800/16, 17; 435/320.1, 325; 536/24.1

(56) References Cited

U.S. PATENT DOCUMENTS

| | | | |
|---|---|---|---|
| 4,873,316 | 10/1989 | Meade et al. | 530/412 |
| 5,965,788 | * 10/1999 | Houdebine et al. | 800/14 |

FOREIGN PATENT DOCUMENTS

| | | |
|---|---|---|
| 0264166 | 4/1988 | (EP) . |
| 0279582 | 8/1988 | (EP) . |
| 9103551 | 3/1991 | (WO) . |

OTHER PUBLICATIONS

Shamay et al., Transgenic Research 1:124–132, 1992.
Kappel et al., Current Opinion in Biotechnology 3:548–553, 1992.
Clark et al., "Pharmaceuticals from transgenic livestock", Tibtech, vol. 5, Jan. 1987, pp. 20–24.
Houdebine, 1994, J. of Biotech. 34:269–287.
Lewin, "Genes", John Wiley and Sons, 1983, p. 182.
Pursel et al., Science 244:1281–1288, 1989.
Devinoy et al., "Recent data on the structure of rabbit . . . hormonal control", Reprod. Nutr. Develop., 28 (4B) 1145–1164, 1988.
Hammer et al., Nature 315 (5021): 680–683, 1985.
Thepot et al, Nucl. Acid Res. 18 (12):3641, 1990.
A.C. Andres et al., "Ha–ras oncogene expression directed by a milk protein gene promoter . . . ", Proceedings of the Nat. Acad. Sciences, vol. 84, Mar. 1987, pp. 1299–1303.
T.A. Buhler et al., "Rabbit beta–casein promoter directs secretion of human interleukin–2 into the milk of transgenic rabbits", Biotech., vol. 8, pp. 140–143, 1990.
C. Puissant et al., "Cortisol induces rapid accumulation of whey acid protein . . . ", Cell Bio. Int'l Reports, vol. 15, No. 2, 2/91, pp. 121–129.
E. Devinory et al., "Sequence of the rabbit whey acid protein cDNA", Nucleic Acids Res., vol. 16, No. 16, Aug. 25, 1988, p. 8180.

* cited by examiner

Primary Examiner—Deborah Crouch
(74) Attorney, Agent, or Firm—Foley & Lardner

(57) ABSTRACT

A transgenic non-human mammal is provided where the genome of the mammal comprises a DNA construct comprising in operable association a rabbit WAP promoter and a DNA sequence encoding a heterologous protein. Methods of using the mammal in the production of recoverable amounts of a heterologous protein in the mammal's milk are discussed and described such that the mammal is a bioreactor for a heterologous protein of interest. Furthermore, cells isolated from the mammal are provided for the production of a heterologous protein of interest in vitro, as well as, DNA constructs of the rabbit WAP promoter for the production of the transgenic non-human mammal.

20 Claims, 13 Drawing Sheets

FIG. 2b pPolyIII-I *

GGATCTGCGGCCGCCTCGAGGGGCCCGGATCCGAATTCCCGGGAGAGCTGATATCGCATGCGGTACC

Figure 1:
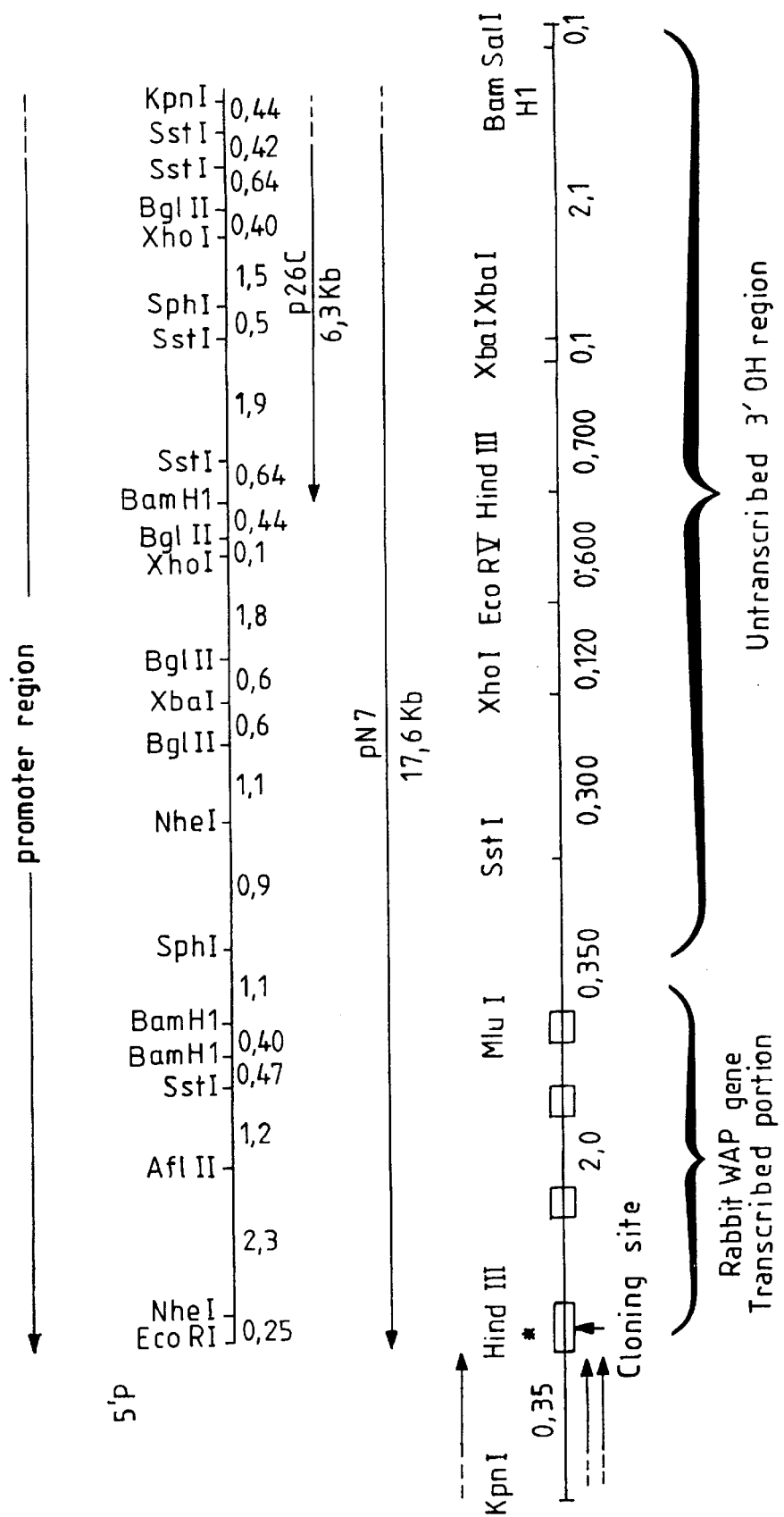

B/B-O  NotI ----- SfiI   BamHI EcoRI SmaI   SstI  EcoRV SphI  KpnI
              NaeI XhoI              AvaI   BanII                BanI

TCTAGAAGAAGCTTGGCCAGCTGGTCGACCTGCAGATCCGGCCCTGAGGCCCGGCGGCCGCAGATCT

XbaI HindIII  PvuII SalI PstI B/B-O    SfiI ------ NotI  BglII
               BalI       AccI                     XhoI NaeI The polylinker of the plasmid p-poly III-I

FIG. 5a

|  |  |
|---|---|
| agatcttgtgctcgctcgctc | -1801 |
| tctcgctctctctctctctccttctgtctctctggaactttgcctttcaaataaataaataattttttttaaa | -1729 |
| agactactgttttgtttttttttatttacttaaagcagagtaacagagaaagaaatacattccgtttgctggt | -1657 |
| tcactccccaaatggccgctagatccagggctaggccaggctgaagccagaaccccctacctgggtctcccac | -1585 |
| gtgagtgacaggggcccaagcacctgggccaaccacctctgctttcccagggacattggcagggagatgggt | -1513 |
| caggagcagagcagccagaactcaggctgccctccaatctgagacatcagctttgcaagtggtagcttaacc | -1441 |
| cacgtgtcacccagccccaagattcatgttaatgataggaaattttaattttatttgctcagattgaaacat | -1369 |
| tataaaggcaccacaataagcagagtccagagatgagagaaaaacaaaaaataaaataaaaaaatcttgtat | -1297 |
| ttcggttcctttgcaggcactttcttcccttttgtggaacaaggagcccaaaaaccgcagcaggggggcccagt | -1225 |
| ggagatgggagatgcctgggaagaacaccctgggaggagctccgggaggcgcaggaggaggggggttcctgac | -1153 |
| ggggtcagctctggcctcgggcccagcaccccagtgagaaggatgggagccgcccagcccagcctggctcgg | -1081 |
| gcaggaaggggcaggcccaaccacagcccctctgctccttcgaagggagcggaacagcccacggaagcatct | -1009 |
| ttcggacttagagccgtgaacctcgccacgccgtgtccagcccactgtctgagagccctcactggccagtcc | - 937 |
| aggcccaggcccaggactctgtgggcagctgcagggctggaacagagttacccgagcctggggctgcgaggg | - 865 |
| gtgcctttgtggaacccacaaaggacgctttgtggaaggacatttggggctggagcctccccacggcacagc | - 793 |

FIG. 5b

| | |
|---|---|
| ctgaggcccaggaagctgcgaggagctctgtgcctgaggccggagcagggtcgctggctggacagggctgtg | -721 |
| gcccccagccatcctgccctggggtctccgcagtccccatggccccttccctgtctgggtcctgggggggcg | -649 |
| ggtgcaggaactacacggccagcagcacatccgcccctgcctgtggcacctgctcccctggcacagggcac | -577 |
| aggagggccttccgagaagagaccttctgtcccctcgcccctccacagtcggcaagcctgcactggggtccc | -505 |
| cagggcaggggcccaggctctgcagtccgcttctcctgtcccctcgcccctccacaggtggcaagcagcaca | -433 |
| ttcttgcttacagagtccagaaaaccacacacacacacacacacacacacacacacacacacaaaaaa | -361 |
| aaacacttgccgacgagacagcccgcacttggtacccgcctcccatgctgcttctcccggctctgagccgtg | -289 |
| ggtacaacccctcggggggggggggggggaggatttctctcccccaccccagtcttcctagcagatgtgcat | -217 |
| cccggccaacatggagggaaatggacaaccttgccggggactttttttttctttcatttgaaaccatgaccgc | -145 |
| agccgttcctccaacctggcctgacctctccacgtgtccaaggaggaagccccctggcccagttgaggcctc | -73 |
| gccaacctggcacccctccaggctcctcctcctgctccaacctttaaatgcatcccggggccccagaacacc | -1 |
| ATCCGACACCTGCCTGCTGCCCACCACCAGCCTACCACCTGCCACC ATG CGC TGT CTC ATC AGC<br>                                                                                                 Met Arg Cys Leu Ile Ser | 64 |
| CTG GCC CTC GGC CTG CTC GCC CTG GAG GCG GCC CTC GCT CTG GCC CCC AAA TTC<br>Leu Ala Leu Gly Leu Leu Ala Leu Glu Ala Ala Leu Ala Leu Ala Pro Lys Phe | 118 |

FIG. 5c

| | |
|---|---:|
| ATC GCT CCA G gtaggcccagctgccttcctcactccgggacgcactcaggaggggtccccttgtctca<br>Ile Ala Pro | 186 |
| tatctgctccagagtccacccaagactcgtggccttggtggctccgtgacagggacacagccggccaggaga | 258 |
| ggagcagaggaggctcacccttgggagggggtcctgggtggcaggaaaccagcgccctgtccccacgcaggg | 330 |
| ggccacgagctgccaggccaaggactggtcacctccggccaggacctgactggcctgctcctgcagtggacc | 402 |
| tgtgtcttgtgtccccacttccacagctgacttcactcgcttttgtcagccgtatcgcagttctggccacgg | 474 |
| gttttttgttttgttttgttttgttttgttttgttttgccctccttcctgggctgctgggggccaggctccca | 546 |
| cggttctgtcctcgccctcctccaaggagccctggggggtgggaggggcagggctgcgggccccccacacactt | 618 |
| gctcgtcctgccccgtgtgcag TG CAG GTC ATG TGC CCC GAG CCC AGC TCT TCC GAG GAG<br>                      Val Gln Val Met Cys Pro Glu Pro Ser Ser Ser Glu Glu | 678 |
| ACG CTC TGC CTC AGT GAC AAC GAC TGT CTC GGC AGC ACC GTG TGC TGT CCC AGC<br>Thr Leu Cys Leu Ser Asp Asn Asp Cys Leu Gly Ser Thr Val Cys Cys Pro Ser | 732 |
| GCC GCC GGC GGC TCC TGC AGA ACC CCC ATC ATC G gtaacgtagccacactgcaggcctct<br>Ala Ala Gly Gly Ser Cys Arg Thr Pro Ile Ile | 792 |
| ccggaagcccacacacctgccccatggcgcagtctctctgggccccatccacctgccccgaggcctctgtgc | 864 |
| caccccacaggtccctgagggctccaggatgccccagtgctgcgggaggtcctgcggtgagaccagcaagag | 936 |

FIG. 5d

| | |
|---|---|
| ggaggccacagagacccagctgacctcaggggtcccccggcgctcaacttgtctcagtggggtcttgcgggt | 1008 |
| caggtctgggggggcccatgttacagggtgtgaccagaaaaggcctgtctctccccag TC CCT ACC CCC<br>                                                                                                                                    Val Pro Thr Pro | 1077 |
| AAG GCT GGC CGC TGC CCC TGG GTG CAG GCG CCA ATG CTG TCC CAG TTG TGT GAG<br>Lys Ala Gly Arg Cys Pro Trp Val Gln Ala Pro Met Leu Ser Gln Leu Cys Glu | 1131 |
| GAG CTG AGC GAC TGT GCC AAC GAC ATC GAG TGC AGG GGC GAC AAG AAG TGC TGC<br>Glu Leu Ser Asp Cys Ala Asn Asp Ile Glu Cys Arg Gly Asp Lys Lys Cys Cys | 1185 |
| TTC AGC CGC TGC GCC ATG CGC TAT CTG GAA CCC ATC CTA G gtatgtgtcctgagccct<br>Phe Ser Arg Cys Ala Met Arg Tyr Leu Glu Pro Ile Leu | 1243 |
| ccccaggcagggctgtcccttcagcagggcccagggctcaggagtggatgtgggtgagtgaagggcactcgg | 1315 |
| ggacgcaggtggcaggcgggacttggccctgggtggctcacaggccagcctgtacctttgccactgatctga | 1387 |
| gagggagtgcagcacagctccaggtatcggaggagtcgaaggttaggagcctgggggtgttgtccaccagctg | 1459 |
| tggcctgcatattccttcctacagaggggggggggcagaggcggggaggggggctctgcttgcgcactagggt | 1531 |
| ccctggcagtgaaccacagccgacactgacctcccaccttgtccccacctgtgtctcctgcag AG   AGC<br>                                                                                                                          Glu  Ser | 1599 |

FIG. 5e

| | |
|---|---|
| ACT CCC CAG TGAGCCGCCTACCCAGGAGTCCCTGGCTGCCAGGAGAGTTGGGCCTGAGTCCCCCTCTTG<br>Thr Pro Gln | 1668 |
| GACCCAGAGAGCTTGTGACGCGTCCTCCCTGCTGCTAATAAAACTACTCAGCTTCA tggctctggttgtct | 1739 |
| Gtccatctgccctgggagcttgggaaaccagtgaccccaagtaggcacagctctgcctggctcagcagccca | 1811 |
| gcacgacgtccgagggaatggactagaccccaagataacgcttacctccctccaccccgtttgagcttgcc | 1883 |
| aggaagggcagcaggccattcagggtgagccacgccctcagggagcccccacgtacctgtgaggtcacttcc | 1955 |
| ctgggcttcagtgcccacgaacccctgtccttttccgtggcagtcagtgaacagagtaagaagaggagagtg | 2027 |
| agctccagcctgtgaagttcagcccttcctgggtgtggcacagagacaggccaggctgtcccaggctgtccc | 2099 |
| aggctgctggccggggggtgcacagaggcctcgcagaagaaagagccatcatgtgcagagtgagaggaaagg | 2171 |
| ccccccagacagaggcatgtgcaggacgcctcggccgggacgtggatcgccagaggcccctgcgcgccatg | 2243 |
| ctggggtgaggggacgtttaggacacagggcctaatggagagcagctaggtcatgggggtgctgcctcctga | 2315 |
| gactggattcgtcccctcgag | 2336 |

TRANSGENIC NON-HUMAN MAMMAL COMPRISING A RABBIT WAP PROMOTER, USES THEREOF, AND A DNA CONSTRUCT COMPRISING THE RABBIT WAP PROMOTER

This application is a continuation of application Ser. No. 08/162,146, filed Feb. 10, 1994.

The present invention relates to a process for the preparation of a protein of interest in the milk of a transgenic animal. It also relates to the constructs which make it possible to obtain these animals, the animals obtained as well as the cells containing the constructs which permit the expression of a heterologous protein.

Several routes have been pursued in order to obtain proteins of biological, therapeutic or industrial interest, and which are naturally produced in small quantities or in a form difficult to purify.

It has thus been possible to produce proteins using genetic recombination techniques, by microorganisms such as bacteria or yeasts. Nevertheless, most of the proteins require, after their synthesis, a maturation stage consisting in chemical modifications of certain reacting groups, glycosylation, and the like. Prokaryotic cells do not have the adequate enzymatic content for carrying out this maturation, hence the production of inactive proteins and/or proteins with high antigenicity.

It is therefore preferable to synthesize these proteins in eukaryotic cells, which will perform the appropriate enzymatic conversions. Nevertheless, the large-scale culture of tissue cells poses a number of technical and economical difficulties.

Another approach therefore consists in causing these proteins to be produced by cells in vivo, using transgenic animals. It is desirable that the system used permits the production of proteins in large quantities and which are easily recoverable. It is therefore advantageous that the recombinant protein is produced in the mammary gland of transgenic animals, and excreted in the milk. It is indeed a biological fluid which can be easily collected, having a relatively limited complexity and a low proteolytic activity; in addition, the processes of maturation of the recombinant proteins will be probably ensured (glycosylation, phosphorylation, cleavage and the like).

Mouse or ewe mammary gland has thus been successfully made to synthesize milk proteins of another species or proteins normally absent from milk (Ref. 1 to 15).

However, the level of proteins thus produced is extremely variable. It is different from one transgenic animal to another, since it is a function of the process of integration of the transgene which is itself variable from one animal to another. The nature of the gene constructs is also essential, the elements regulating the expression of the milk protein genes being possibly many and situated at various points of the promoter region and the transcribed portion of the gene. Thus, the promoters of ovine beta-lactoglobulin, of rat WAP and of rat beta-casein are capable of causing these proteins to be synthesized in transgenic mice. The levels are, however, systematically high only in the case of beta-lactoglobulin. Likewise, the beta-lactoglobulin promoter directs the synthesis of human alpha$_1$-antitrypsin which reaches the value of 7 mg/ml of milk in the milk of a transgenic mouse. The alpha$_{S1}$-casein promoter permits the synthesis of human urokinase, but the promoters of the rat beta-casein and rabbit beta-casein genes used up until now are of a limited activity. The promoter of the mouse WAP gene directs the synthesis of several foreign proteins (plasminogen activator, CD4) which are secreted in the milk of transgenic mice. The quantities of proteins obtained with this promoter are however relatively small.

Furthermore, it may happen that the specificity of the promoter is modified by its association with a foreign gene. In this way Gunzburg et al. (Molecular Endocrinology 1991) obtain the secretion of growth hormone by means of a recombinant DNA under the dependence of the mouse WAP promoter, in transgenic animals; but the growth hormone is, in this case, also produced in the cerebellum, in Bergman glial cells. Such phenomena can result in toxicity and in the premature death of the animal.

The present invention is based on the demonstration of the special interest of the promoter of the rabbit WAP gene. Indeed, the rabbit WAP ("whey acidic protein") is a relatively abundant rabbit milk protein (15 mg/ml of milk), and rabbits are potentially transgenic animals which can be used on a large scale.

The present invention relates to a process for the preparation of a heterologous protein of interest in mature form or in fused form in the milk of a mammalian female, in which process:

said female is bred and, the milk is recovered and said protein is recovered from it and is separated if necessary, characterized in that said female is a transgenic animal in the genome of which has been integrated a sequence encoding said protein of interest under the control of at least one sequence present among the elements for expression of the rabbit WAP protein and situated on the fragment having a length of at least 3 Kb from the 3' end of the complete WAP promoter.

Preferably, the present invention relates to a process in which the sequence controlling the expression of the protein of interest comprises, in addition, expression elements situated on the fragment between 3 Kb and 6.3 Kb from the 3' end of the WAP promoter.

The production of transgenic animals is known and has been widely described with similar constructs in the documents mentioned above, but also in Günzburg et al., Hennighausen et al., Burdon et al., Reddy et al. as well as in Patent WO 90 05188.

The detailed description of the methods of transgenesis will not be repeated in detail, the above documents are incorporated in the present description by direct reference.

"Heterologous protein of interest" is understood to essentially designate a protein which is not naturally under the control of the rabbit WAP promoter.

In the process according to the invention, the mammalian female used is preferably a rabbit, but these constructs are also effective in other mammalians, for example mice.

The milk obtained contains the protein of interest which can be isolated or otherwise, and then, according to whether it is in mature of fused form, it can be subjected to a chemical or enzymatic cleavage if necessary.

The DNA constructs used are preferably introduced by microinjection into fertilized egg at the one cell up to the 8 cell stage, and then the animals corresponding to the criteria described above, that is to say transgenic and expressing said protein in the milk, are selected.

The promoter region of this WAP gene, grafted on to the reporter gene for bacterial chloramphenicol acetyl transferase (CAT) contains the elements sensitive to the two most important lactogenic hormones, prolactin and glucocorticoids. These hormones intensely stimulate the expression of the CAT gene when the hybrid gene is transfected into rabbit mammary primary epithelial cells. The hormone response depends on the length of the promoter used. The promoter of the rabbit WAP gene is therefore much more effective than the promoters of the mouse and rat WAP genes used up until now.

In particular, in the process according to the present invention, the sequence encoding the protein of interest can be preceded toward its 5' end, by a sequence corresponding to the promoter of the complete rabbit WAP gene, or by an equivalent sequence, which ensures the function of the promoter. It is even possible, in this case, to use the entire WAP gene and a WAP promoter of said gene or of an equivalent sequence. The FIG. 5 accompanying the present application represents said rabbit WAP gene.

"Equivalent sequence" is understood to preferably designate a sequence having at least a length of 3 Kb from the 3' end of the WAP promoter and in particular comprising the expression elements situated on the fragment with a length of at least 6.3 Kb from the 3' end of the complete rabbit WAP promoter, especially situated between the HindIII and BamHI sites (FIG. 1).

The promoter may contain a 17-Kb sequence between the HindIII and EcoRI sites, or a sequence containing the expression elements situated on this fragment. The essential elements of the constructs according to the invention are situated on the fragment with a length of 17.6 Kb from the 3' end of the promoter.

This long promoter is capable of providing elements which further promote the expression of the foreign gene which is attached to it, or of making its expression more regularly high by making them more independent of the site of insertion of the transgene into the genome.

The 6.3 Kb short promoter will give a response to the lactogenic hormones which is practically identical to that obtained with the 17 Kb long promoter, and can direct the synthesis of proteins, whose genes are associated with it in a vector, at very high levels.

The invention also relates to constructs as defined above but in which, in the sequence corresponding to the rabbit WAP protein gene, the initiator AUG codon is deleted.

This modification can be obtained especially by site-directed mutagenesis.

When the sequence encoding the protein of interest is in a form fused with the sequence of all or part of the WAP gene, it is possible to suppress the ATG sequence of this protein.

The rabbit WAP protein can thus, with this type of construct, be expressed for example in tranagenic mice.

In this type of construct comprising the rabbit WAP protein gene, which may have lost the initiator AUG codon, the gene or cDNA for the protein of interest can be placed at different sites which may result in different levels and types of constructs, as will emerge from the examples.

According to another of its aspects, the present invention provides a process for recovering the milk produced by a mammalian female and the protein which it contains, characterized in that, in order to recover the protein of interest from the milk of said mammalian female, a) the mammary glands are recovered,
b) the mammary glands are incubated at a temperature of about 0° C. for a period ranging from two hours to 18 hours,
c) the milk having spontaneously exuded from the glands is recovered,
d) the protein of interest is isolated from the milk and said purified protein is obtained.

This process was developed within the framework of the production of a heterologous protein by a transgenic animal having integrated into its genome fragments of the WAP protein gene, but it can be applied to the purification of any protein which it is desired to isolate from milk.

It represents a considerable advantage compared with conventional processes for milking non-ruminant mammalians, with respect to the quantities obtained, especially for small animals such as mice (24). The composition of the milk recovered is identical to that of the milk produced naturally. This process permits, in addition, an easier transfer of the products obtained from the site of production to the site of purification and treatment, by transporting the mammary glands in ice.

The process for the preparation of heterologous protein of the present invention, according to anyone of its variants, makes it possible to obtain a large number of proteins. Among these proteins, there should be mentioned:
  growth factors,
  interleukins,
  stimulating factors,
  kinases,
  coagulation factors,
  alpha-antitrypsin,
  hirudin, and in particular:
    erythropoietin,
    G-CSF,
    alpha-antitrypsin,
    urokinase,
    factor VIII.

The following constructs can be mentioned:
  WAP-human alpha$_1$-antitrypsin construct (Arg 358 analog): the entire human alpha$_1$-antitrypsin gene having Arg 358 in place of Meth 358 (Courtney, Bull. Inst. Pasteur (1988) 86, 85–94) was fused to the long promoter (17.6 Kb) of the rabbit WAP gene at the HindIII site of the untranslated S'P sequence, on the model of the WAP-GH constructs. Several mouse lines express the human gene at the concentration of 2 and 5 mg/ml of milk.
  WAP-human erythropoietin construct: the entire human erythropoietin gene (Semenza et al., Proc. Natl. Acad. Sci. USA (1989) 86, 2301–2305) is fused to the promoter (6.3 Kb and 17.6 Kb) of the rabbit WAP gene.
  WAP-human factor VIII-deltaII construct: the cDNA of the human factor VIII-deltaII (deleted from the B region [Meulien et al., Prot. Engin (1988) 2, 301–306]) preceded by the first intron of the factor VIII gene and lacking its polyadenylation sequence, was introduced inside the entire rabbit WAP gene at the HindIII site introduced by site-directed mutagenesis and which precedes the natural AUG.

The constructs according to the invention make it possible to obtain completely unexpected results, in particular, the 6.3 Kb promoter of WAP combined with the human and bovine growth hormone genes is capable of directing the synthesis of these proteins in tranegenic mouse milk at very high levels (1–21 mg/ml).

The hGH contained in the milk of the transgenic mice is structurally intact. The hGH also conserved its biological activity (evaluated not by its growth hormone activity but by its prolactin activity). The biological test indicates that the concentration of the hormone is 10 mg/ml, a value which is in agreement with the values found by the radioimmunological test and by electrophoresis.

The promoter of the rabbit WAP gene is therefore much more effective than the promoters of the mouse and rat WAP genes used up until now.

Table 1 below gives a summary of the results of publications 2 to 15 and therefore projects the advantages of the results obtained with the constructs according to the invention relative to those published in the prior art.

TABLE 1

Summary of the different recombinant proteins expressed in the milk of transgenic animals.

| Promoter used | Protein encoded | Animal used | Number of animals expressing the protein in milk | Concentration of the protein in milk in microgram/ml |
|---|---|---|---|---|
| Bovine alpha-casein | Human urokinase | Mouse | 1 out of 3 | 1000 |
| Rabbit beta-casein | Human interleukin-2 | Rabbit | 4 out of 4 | 0.001 to 0.01 |
| Ovine beta-lacto-globulin | Human coagulation factor IX | Ewe | 2 out of 2 | 0.01 |
| Ovine beta-lacto-globulin | Human alpha$_1$-anti-trypsin | Ewe | 2 out of 2 | 5 |
| | | Mouse | 7 out of 13 | 6 to 7000 |
| Mouse WAP | Human cD4 [sic] | Mouse | 5 out of 7 | 0.4 |
| Mouse WAP | Human tPA | Mouse | 4 out of 6 | 0.08 to 50 |
| Mouse WAP | Protein PS2 | Mouse | 1 out of 1 | 1.5 |
| Mouse WAP | Human GH | Mouse | 8 out of 8 | 1000 |
| Rabbit short WAP | Human GH | Mouse | 6 out of 6 | 5 to 21,000 |
| Rabbit short WAP | Bovine GH | Mouse | 8 out of 8 | 1200 to 16,700 |
| Rabbit long WAP | Bovine GH | Mouse | 4 out of 4 | 87 to 6900 |

One of the essential reasons may consist in the fact that the rabbit DNA fragment (6.3 Kb) was much longer than its mouse and rat homolog (2.6 Kb and 0.9 Kb). Essential regulatory elements can be missing in the mouse and rat DNA fragments used.

The present invention also relates to the constructs which make it possible to obtain transgenic animals according to the invention.

The present invention relates especially to the DNA sequences and the vectors which make it possible to implement the process; in particular the DNA sequences comprising at least one heterologous gene encoding a protein of interest, under the control of at least one sequence present among the elements for expression of the rabbit WAP protein and located on the fragment having a length of at least 3 Kb from the 3' end of the complete WAP promoter.

The present invention also relates to transgenic animals which can be used in the process according to the present invention, as well as transformed cells containing the constructs according to the invention.

Although the animals in question can be very different, rabbits are animals which can be potentially used to obtain recombinant proteins in abundance. Up to 100 ml of milk can be collected each day. This milk is highly rich in proteins (much richer than the milk of ruminants). It is moreover easier and less costly to obtain rabbits than large transgenic animals. The promoter of the rabbit WAP gene has, furthermore, every chance of best directing the synthesis of recombinant proteins in rabbits.

Other characteristics and advantages of the present invention invention [sic] will emerge on reading the examples below in which reference is made to the following figures:

FIG. 1: Map of the rabbit WAP gene.

Figure 2A:
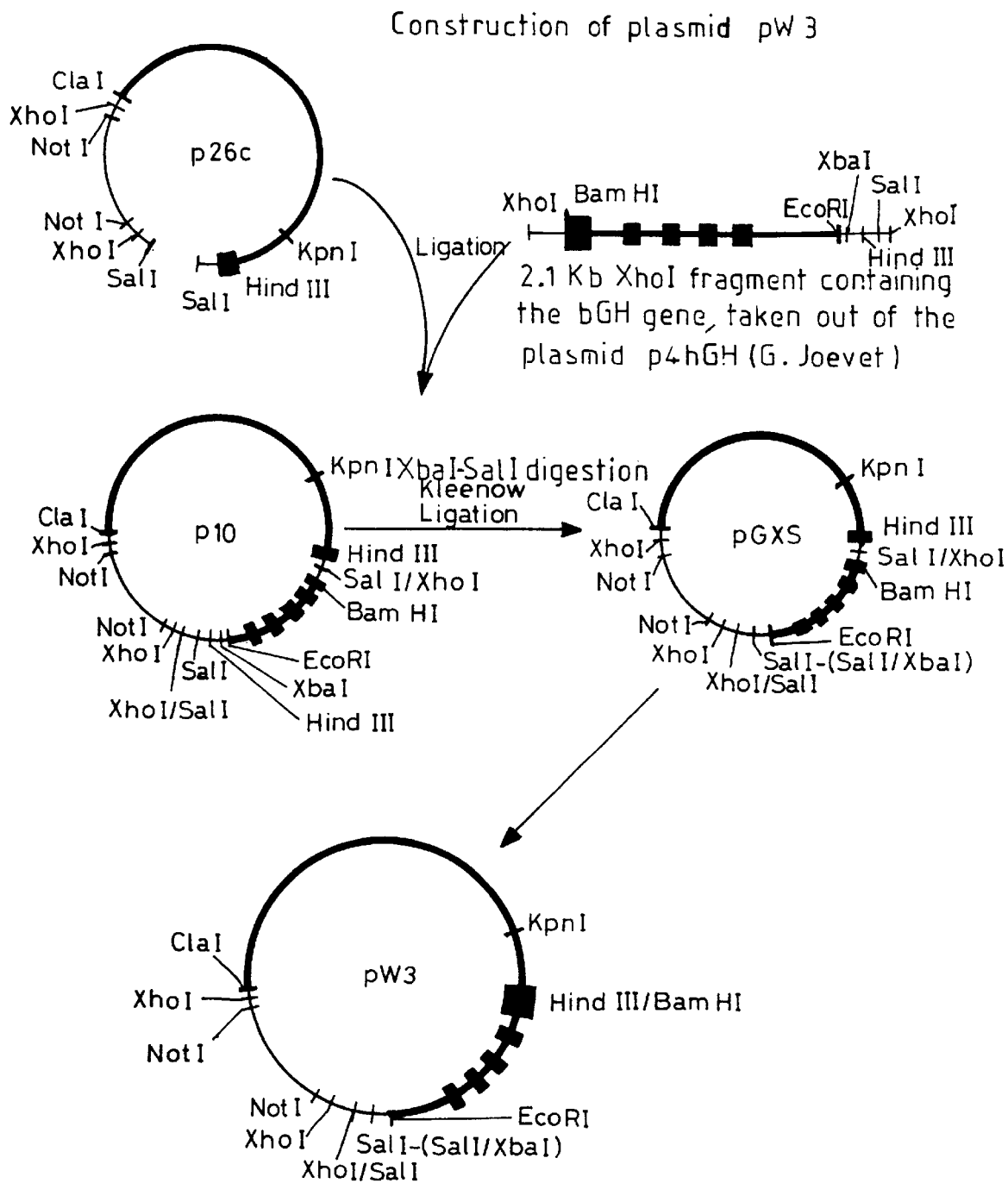

FIG. 2a: Schematic representation of the construction of the plasmid pW$_3$.

FIG. 2b: Polylinker of the plasmid p-polyIII-I-(SEQ ID NO:1)

Figure 3:
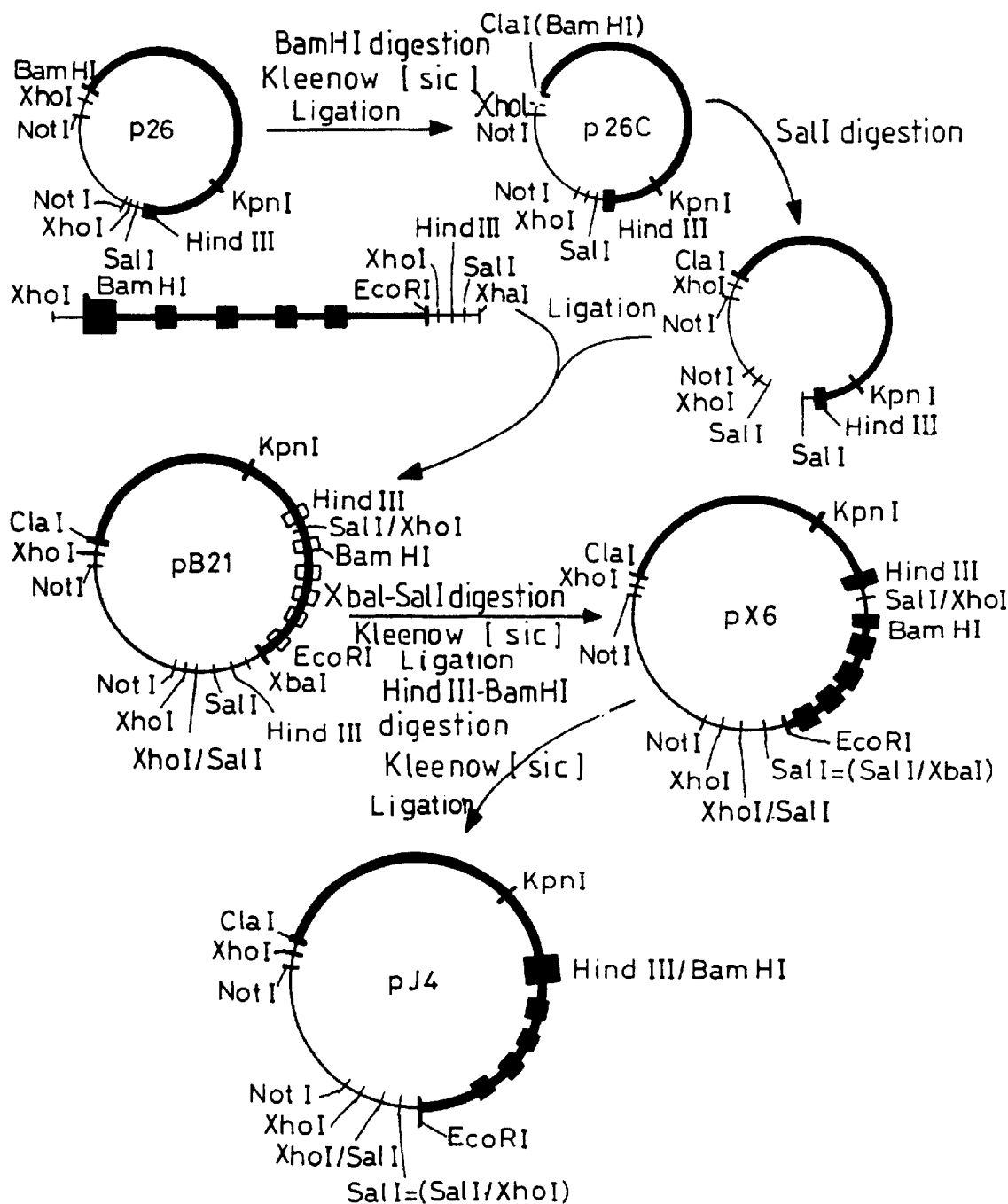

FIG. 3: Schematic representation of the construction of the plasmid pJ$_4$.

Figure 4:
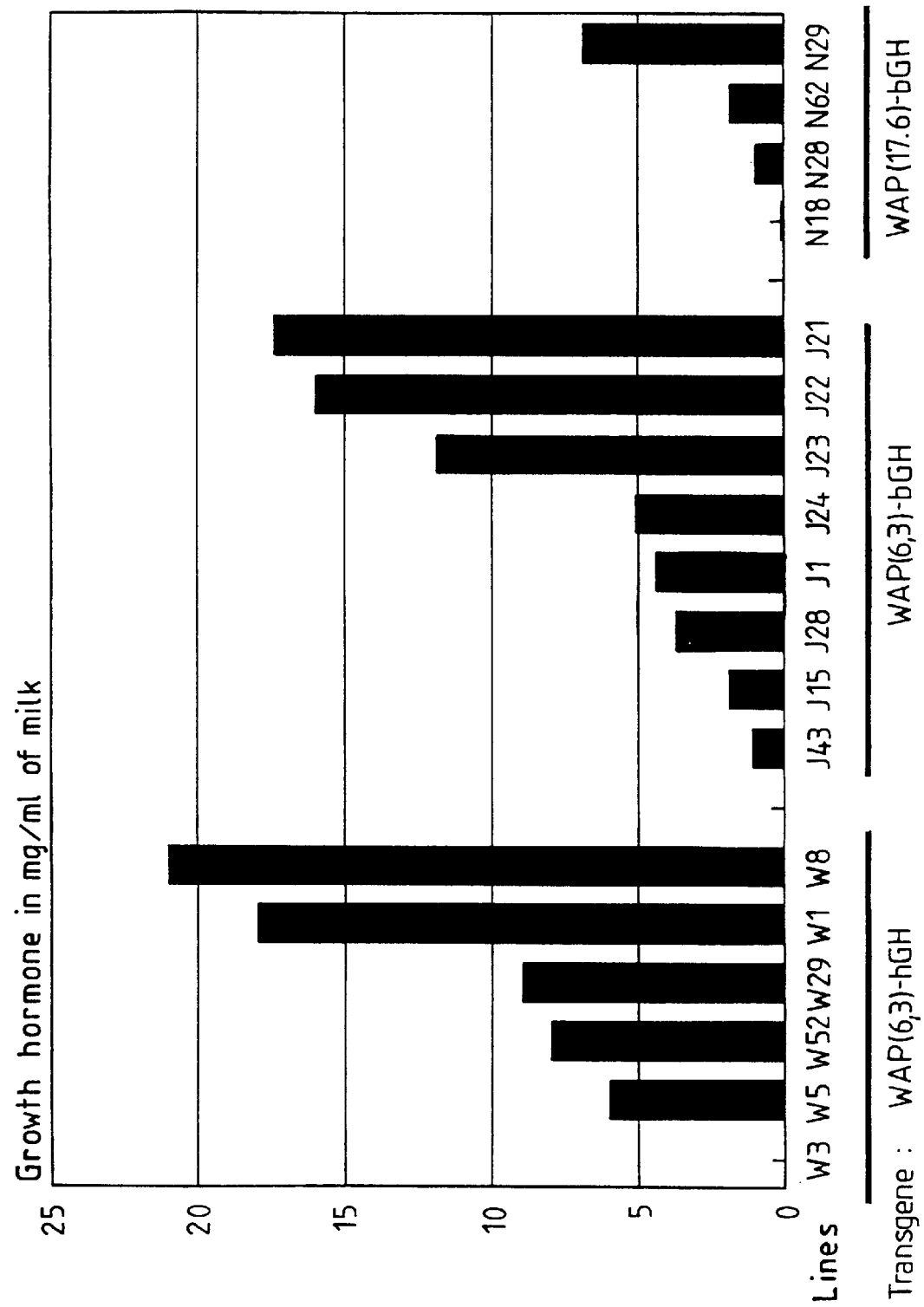

FIG. 4: Production of human and bovine growth hormone in transgenic mouse lines harboring the constructs pW$_3$ and pJ$_4$.

FIG. 5: Sequence of the rabbit WAP gene (SEQ ID NOS 2–3).

Figure 6:
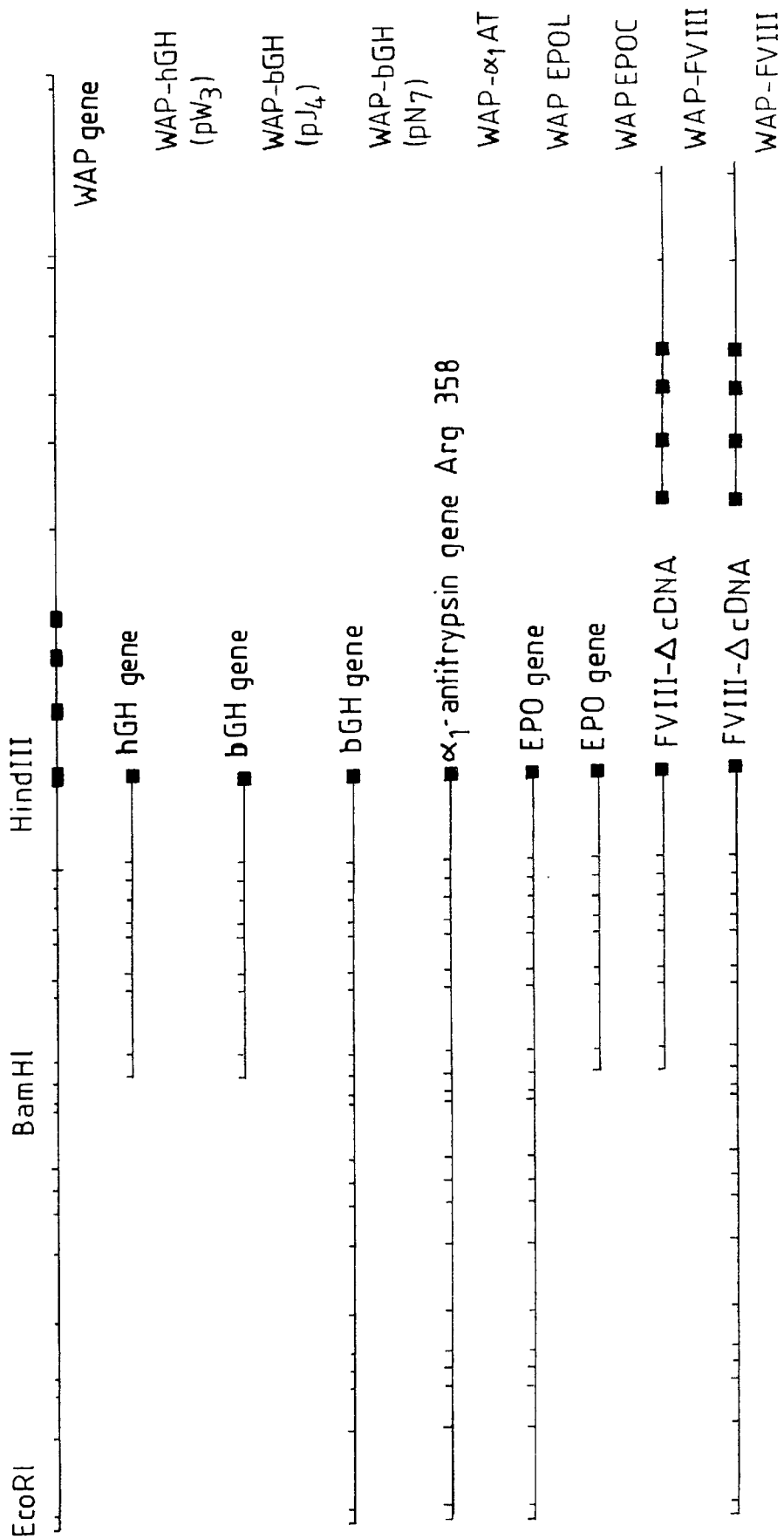

FIG. 6: Schematic representations of the different constructs used in vivo.

Figure 7:
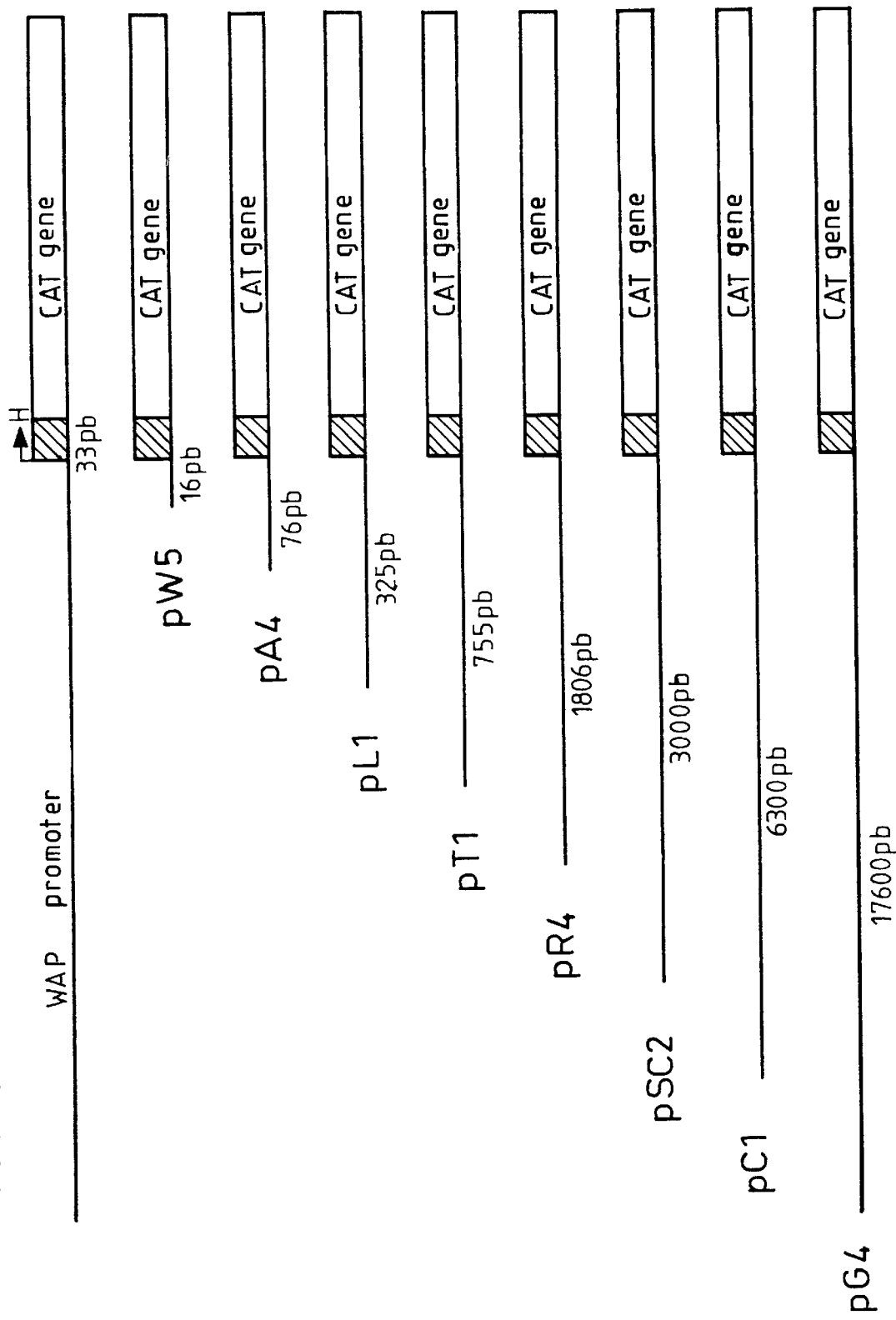

FIG. 7: Schematic representations of the constructs containing the CAT reporter gene and variable lengths of the promoter WAP.

Figure 8:
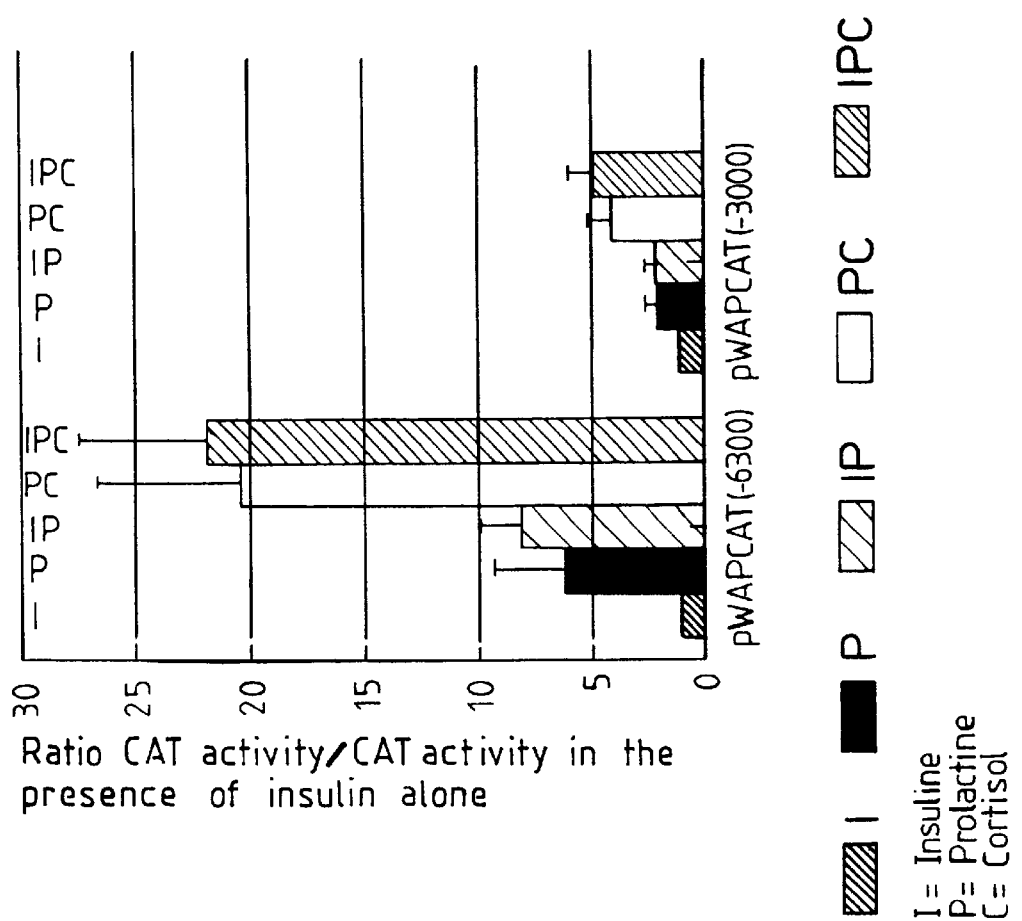

FIG. 8: Efficiency of the constructs described in FIG. 7.

EXAMPLE 1

Construction of the Plasmid pW$_3$

The plasmid p26C is first prepared.

The plasmid p26C was obtained by introducing the BamH$_1$-HindIII sequence of the WAP gene (6.3 Kb fragment of FIG. 1) into the polylinker of the p-polyIII-I vector (between the BamH$_1$ [sic] and HindIII sites).

During this cloning, the BamH$_1$ [sic] site was suppressed and replaced by the ClaI site which is present in the vector p26C (FIG. 2). The vector p26C is therefore a plasmid capable of receiving a foreign gene placed under the dependency of the 6.3 Kb WAP promoter. The introduction of the foreign gene can be carried out for example in the SalI site of the polylinker (FIG. 2). The inserts containing the entire promoter and foreign genes can be isolated from the plasmid after cutting at the two NotI sites which are at the ends of the polylinker of the plasmid p-polyIII-I.

The plasmid pW$_3$ obtained from the plasmid p26C (according to FIG. 2) contains the promoter of the rabbit WAP gene (6.3 Kb) and the human growth hormone gene (hGH). The fragment used to obtain the transgenic mice is between the two NotI sites.

A HindIII site was introduced into the leader sequence of the gene by site-directed mutagenesis so as to serve as cloning site.

EXAMPLE 2

Construction of the Plasmid pJ$_4$

The plasmid pJ$_4$ obtained from the plasmid p26 (according to FIG. 3) contains the promoter of the rabbit WAP gene (6.3 Kb) and the bovine growth hormone gene (bGH). The fragment used to obtain the transgenic mice is between the two NotI sites.

The *E. coli* strain containing the plasmid p26 was deposited on Jun. 12, 1991, under the number I-1116 at the Collection Nationale de Culture de Microorganisms of Institut Pasteur, 25 rue du Docteur Roux, 75724 PARIS CEDEX 15.

EXAMPLE 3

Production of Transgenic Mice

The $pW_3$ and $pJ_4$ fragments were used to obtain transgenic animals. Transgenic mice were obtained by the conventional technique of microinjection (Brinster et al., Proc. Natl. Acad. Sci. USA (1985) 82, 4438–4442). 1–2-pl containing 500 copies of the gene were injected into the male pronucleus of mouse embryos. The constructs were prepared in the vector p-polyIII-I (Lathe et al., Gene (1987) 57, 193–201). The NotI-NotI fragments of this vector containing the recombinant genes were microinjected. The embryos were then transferred into the oviduct of hormonally prepared adoptive females. About 10% of the engineered embryos gave birth to young mice and 2–5% of the engineered embryos to transgenic young mice. The presence of the transgenes was revealed by the technique of Southern blotting from the DNA extracted from the mouse tails. The concentrations of growth hormone in the blood and in the milk of the animals were evaluated by means of specific radioimmunological tests.

The biological activity of the hGH was evaluated by adding milk to the culture medium of cells or of mammary explants of rabbits. The hGE content in the milk induced the expression of the β-casein gene evaluated by the measurement of the mRNAs and the protein.

EXAMPLE 4

Production of Hunan or Bovine Growth Hormone in the Milk of Transgenic Mice Having Incorporated the Constructs pW3 and pJ4

The hormone concentrations were determined by specific radioimmunological tests.

The identification of hGH in the milk of a transgenic mouse is carried out in the following manner. The mouse milk is centrifuged at 150,000 g for one hour in order to sediment the casein micelles. The supernatant (1 µl per well) was recovered and examined by polyacrylamide gel electrophoresis in the presence of control human growth hormone and a control milk. The results are reported in FIG. 4.

The animals having integrated the construct $pW_3$ give hGH concentrations of the order of 10 mg/ml of milk and can reach 21 mg/ml.

The animals having integrated the construct $pJ_4$ produce of the order of 5 mg of bGH/ml of milk and up to 17 mg/ml.

The process according to the present invention makes it possible to harvest 1.5 ml of milk/mouse maamary gland (by placing the mamary gland in ice). 200 suckling mice expressing a foreign protein at the concentration of 3–5 mg/ml therefore provide 1 g of crude protein.

EXAMPLE 5

Gene Constructs

The gene constructs used for expressing recombinant proteins in the milk of transgenic animals contain in all cases the regulatory region of the rabbit WAP gene: BamHI-HindIII fragment (6.3 Kb) or EcoRI-HindIII fragment (17.6 Kb). The plasmids WAP-hGH, WAP-bGH, WAP-α-AT, and WAP-EPO contain the entire genes (leader sequence, exons, introns, and transcription terminator) of the human growth hormone (hGH), of the bovine growth hormone (bGH), of the human $α_1$-antitrypsin mutated at Arg 358 and of human erythropoietin, respectively. In these constructs, the genes were associated with the regulatory region of the WAP gene at the HindIII site. The construct WAP-FVIII-ΔII contains the cDNA of human factor VIII in its Δ II form preceded by an intron of the human factor VIII gene. This intron-CDNA assembly was introduced into the HindIII site of the entire rabbit WAP gene (FIG. 6).

EXAMPLE 6

Identification of the Activity of the Regulatory Region of the Rabbit Wap Gene in Vitro The variable lengths of the region situated upstream of the transcription initiation site of the WAP gene were combined with a reporter gene (the CAT gene: chloramphenicol acetyl transferase) (FIG. 7). These constructs were introduced into mammary epithelial cells cultured on a rat tail collagen I gel by transfection by means of lipofectin. The cells were then maintained for three days in the presence of hormones (insulin, cortisol, prolactin). The enzyme was then measured in the cellular extracts. The constructs containing only 1806 bp or less of the regulatory region do not express the CAT gene. The construct containing 3000 bp is weakly active while the constructs containing 6300 and 17,600 bp are clearly expressed in the presence of the hormones. Prolactin alone exerts a weak but significant inducing role on the CAT gene. Insulin and especially cortisol, which are inactive alone, amplify the action of prolactin. The sensitivity of the gene toward the hormones is exactly identical to that of the endogenous WAP gene of the cells. The −3000–1806 bp and −6300–3000 bp regions therefore contain the regulatory elements essential for the WAP gene to be intensely expressed (FIG. 8). The 17,600–6300 bp fragment does not provide additional stimulation in vitro, which does not rule out that it can have such an action in vitro in transgenic animals. These experiments reveal for the first time the activity of the regulatory regions of the WAP gene in vitro via transfections of the cells.

REFERENCES

1. VAN BRUNT J. Biotechnology (1988) 6, 1149–1154
2. SIMONS J. P. et al. Nature (1987) 328, 530–532
3. SIMONS J. P. et al. Biotechnology (1988) 6, 179–183
4. CLARK A. J. Biotechnology (1989) 7, 487–492
5. ARCHIBALD A. L. et al. Proc. Natl. Acad. Sci. USA (1990) 87, 5178–5182
6. HARRIS et al. J. Reprod. Fert. (1990) 88, 707–715
7. GORDON K. et al. Biotechnology (1987) 5, 1183–1187
8. PITTIUS C. W. Proc. Natl. Acad. Sci. USA (1988) 85, 5874–5878
9. PITTIUS C. W. et al. Mol. Endocr. (1988) 2, 1027–1032
10. YU S. H. et al. Mol. Biol. Med. (1989) 6, 255–261
11. LEE K. F. Nucleic Acids Res. (1989) 16, 1027–1040
12. MEADE H. Biotechnology (1990) 8, 443–446
13. BUHLER T. A. Biotechnology (1990) 8, 140–143
14. VILOTTE J. L. Em. J. Biochem. (1989) 186, 43–48
15. BAYNA E. M. et al. Nucleic Acids Res. (1990) 18, 2977–2985
16. LEE K. F. et al. Mol. Cell Biol. (1989) 9, 560–565
17. GRABOWSKI H. et al. (submitted for publication)
18. DEVINOY E. et al. Nucleic Acids Res. (1988) 16, 11814
19. THEPOT D. et al. Nucleic Acids Res. (1990) 18, 3641

20. GUNZBURG W. H. et al. Molecular Endocrinology (1991). A mammary-specific Promoter Directs Expression of Growth Hormone not only to the Mammary Gland, but also to Bergman Glia cells in Transgenic Mice.
21. HENNIGRAUSEN L. Protein Expression and Purification (1990) 1, 3–8
22. BURDON T. et al. Expression of a whey acidic protein transgene during mammary development: Evidence for different mechanisms of regulation during pregnancy and lactation
23. REDDY B. V. et al. Human Growth Hormone Expression in Transgenic Mouse Milk, abstract in Transgenes, Development and Disease. p.212
24. MASCHIO A. et al. (1991) Biochem. J. 275 454–467

LEGEND TO THE FIGURES

FIG. 6:

The constructs used to obtain the expression of recombinant proteins in the milk of transgenic animals.

FIG. 7:

Schematic representation of the different constructs containing the CAT gene placed under the dependence of variable lengths of the rabbit WAP gene.

FIG. 8:

Representation of the variation of the CAT activity in extracts of rabbit mammary primary epithelial cells transfected with different plasmids.

What is claimed is:

1. A transgenic non-human transgenic mammal whose genome comprises a DNA construct comprising in operable association a rabbit WAP promoter and a DNA sequence encoding a heterologous protein, wherein said rabbit WAP promoter has a length of between 3.0 to 6.3 kilobases extending upstream from the transcription initiation site defined as nucleotide 1822 of the DNA sequence of the rabbit WAP gene depicted in SEQ. ID. NO: 2, and wherein said mammal expresses said DNA sequence such that a recoverable amount of said heterologous protein is produced in the milk of said mammal.

2. A transgenic non-human transgenic mammal whose genome comprises a DNA construct comprising in operable association a rabbit WAP promoter and a DNA sequence encoding a heterologous protein, wherein said rabbit WAP promoter has a length of 6.3 kilobases extending upstream from the transcription initiation site defined as nucleotide 1822 of the DNA sequence of the rabbit WAP gene depicted in SEQ. ID. NO: 2, and wherein said mammal expresses said DNA sequence such that a recoverable amount of said heterologous protein is produced in the milk of said mammal.

3. The transgenic non-human transgenic mammal of claim 2, wherein said rabbit WAP promoter is the 6.3 kilobase HindIII-BamHI restriction fragment depicted in FIG. 1.

4. A transgenic non-human transgenic mammal whose genome comprises a DNA construct comprising in operable association a rabbit WAP promoter and a DNA sequence encoding a heterologous protein, wherein said rabbit WAP promoter has a length of 17.6 kilobases extending upstream from the transcription initiation site defined as nucleotide 1822 of the DNA sequence of the rabbit WAP gene depicted in SEQ. ID. NO: 2, and wherein said mammal expresses said DNA sequence such that a recoverable amount of said heterologous protein is produced in the milk of said mammal.

5. The transgenic non-human transgenic mammal of claim 4, wherein said rabbit WAP promoter is the HindIII-EcoRI restriction fragment depicted in FIG. 1.

6. An isolated mammalian cell comprising a genome which comprises a DNA construct comprising in operable association a rabbit WAP promoter and a DNA sequence encoding a heterologous protein, wherein said rabbit WAP promoter has a length of between 3.0 to 6.3 kilobases extending upstream from the transcription initiation site defined as nucleotide 1822 of the DNA sequence of the rabbit WAP gene depicted in SEQ. ID. NO: 2.

7. The mammalian cell as claimed in claim 6, wherein said cell is a mammary epithelial cell.

8. An isolated mammalian cell comprising a genome which comprises a DNA construct comprising in operable association a rabbit WAP promoter and a DNA sequence encoding a heterologous protein, wherein said rabbit WAP promoter has a length of 6.3 kilobases extending upstream from the transcription initiation site defined as nucleotide 1822 of the DNA sequence of the rabbit WAP gene depicted in SEQ. ID. NO: 2.

9. The mammalian cell as claimed in claim 8, wherein said cell is a mammary epithelial cell.

10. The mammalian cell as claimed in claim 8, wherein said rabbit WAP promoter is the 6.3 kilobase HindIII-BanHI restriction fragment depicted in FIG. 1.

11. The mammalian cell as claimed in claim 10, wherein said cell is a mammary epithelial cell.

12. An isolated mammalian cell comprising a genome which comprises a DNA construct comprising in operable association a rabbit WAP promoter and a DNA sequence encoding a heterologous protein, wherein said rabbit WAP promoter has a length of 17.6 kilobases extending upstream from the transcription initiation site defined as nucleotide 1822 of the DNA sequence of the rabbit WAP gene depicted in SEQ. ID. NO: 2.

13. The mammalian cell as claimed in claim 12, wherein said cell is a mammary epithelial cell.

14. The mammalian cell as claimed in claim 12, wherein said rabbit WAP promoter is the HindIII-EcoRI restriction fragment depicted in FIG. 1.

15. The mammalian cell as claimed in claim 14, wherein said cell is a mammary epithelial cell.

16. A DNA construct comprising in operable association a rabbit WAP promoter and a DNA sequence encoding a heterologous protein, wherein said rabbit WAP promoter has a length of between 3.0 to 6.3 kilobases extending upstream from the transcription initiation site as defined as nucleotide 1822 of the DNA sequence of the rabbit WAP gene depicted in SEQ. ID. NO: 2.

17. A DNA construct comprising in operable association a rabbit WAP promoter and a DNA sequence encoding a heterologous protein, wherein said rabbit WAP promoter has a length of 6.3 kilobases extending upstream from the transcription initiation site defined as nucleotide 1822 of the DNA sequence of the rabbit WAP gene depicted in SEQ. ID. NO: 2.

18. The DNA construct as claimed in claim 17, wherein said rabbit WAP promoter is the 6.3 kilobase HindIII-BamHI restriction fragment depicted in FIG. 1.

19. A DNA construct comprising in operable association a rabbit WAP promoter and a DNA sequence encoding a heterologous protein, wherein said rabbit WAP promoter has a length of 17.6 kilobases extending upstream from the transcription initiation site defined as nucleotide 1822 of the DNA sequence of the rabbit WAP gene depicted in SEQ. ID. NO: 2.

20. The DNA construct as claimed in claim 19, wherein said rabbit WAP promoter is the HindIII-EcoRI restriction fragment depicted in FIG. 1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 137 base pairs
      (B) TYPE: nucleic acid
      (C) STRANDEDNESS: double
      (D) TOPOLOGY: linear (xi) SEQUENCE DESCRIPTION: SEQ ID NO:1:

```
GGATCTGCGG CCGCCGGCCT CGAGGGCCGG ATCCGAATTC CCGGGAGAGC TCGATATCGC      60

ATGCGGTACC TCTAGAAGAA GCTTGGCCAG CTGGTCGACC TGCAGATCCG GCCCTCGAGG     120

CCGGCGGCCG CAGATCT                                                    137
```

(2) INFORMATION FOR SEQ ID NO:2:

(i) SEQUENCE CHARACTERISTICS:
      (A) LENGTH: 4157 base pairs
      (B) TYPE: nucleic acid
      (C) STRANDEDNESS: double
      (D) TOPOLOGY: linear (ix) FEATURE:
      (A) NAME/KEY: CDS
      (B) LOCATION: join(1868..1949, 2462..2587, 2888..3046, 3416
         ..3429)

(xi) SEQUENCE DESCRIPTION: SEQ ID NO:2:

```
AGATCTTGTG CTCGCTCGCT CTCTCGCTCT CTCTCTCTCT CCTTCTGTCT CTCTGGAACT      60

TTGCCTTTCA AATAAATAAA TAATTTTTTT AAAAGACTAC TGTTTTGTTT TTTTTATTTA     120

CTTAAAGCAG AGTAACAGAG AAAGAAATAC ATTCCGTTTG CTGGTTCACT CCCCAAATGG     180

CCGCTAGATC CAGGGCTAGG CCAGGCTGAA GCCAGAACCC CTACCTGGGT CTCCCACGTG     240

AGTGACAGGG GCCCAAGCAC CTGGGCCAAC CACCTCTGCT TTCCCAGGGA CATTGGCAGG     300

GAGATGGGTC AGGAGCAGAG CAGCCAGAAC TCAGGCTGCC CTCCAATCTG AGACATCAGC     360

TTTGCAAGTG GTAGCTTAAC CCACGTGTCA CCCAGCCCCA AGATTCATGT TAATGATAGG     420

AAATTTTAAT TTTATTTGCT CAGATTGAAA CATTATAAAG GCACCACAAT AAGCAGAGTC     480

CAGAGATGAG AGAAAAACAA AAAATAAAAT AAAAAAATCT TGTATTTCGG TTCCTTTGCA     540

GGCACTTTCT TCCCTTTGTG GAACAAGGAG CCCAAAAACC GCAGCAGGGG GCCCAGTGGA     600
```

```
                                                          -continued

GATGGGAGAT GCCTGGGAAG AACACCCTGG GAGGAGCTCC GGGAGGCGCA GGAGGAGGGG        660

GTTCCTGACG GGGTCAGCTC TGGCCTCGGG CCCAGCACCC CAGTGAGAAG GATGGGAGCC        720

GCCCAGCCCA GCCTGGCTCG GGCAGGAAGG GGCAGGCCCA ACCACAGCCC CTCTGCTCCT        780

TCGCAGGGAG CGGAACAGCC CACGGAAGCA TCTTTCGGAC TTAGAGCCGT GAACCTCGCC        840

ACGCCGTGTC CAGCCCACTG TCTGAGAGCC CTCACTGGCC AGTCCAGGCC CAGGCCCAGG        900

ACTCTGTGGG CAGCTGCAGG GCTGGAACAG AGTTACCCGA GCCTGGGGCT GCGAGGGGTG        960

CCTTTGTGGA ACCCACAAAG GACGCTTTGT GGAAGGACAT TTGGGGCTGG AGCCTCCCCA       1020

CGGCACAGCC TGAGGCCCAG GAAGCTGCGA GGAGCTCTGT GCCTGAGGCC GGAGCAGGGT       1080

CGCTGGCTGG ACAGGGCTGT GGCCCCCAGC CATCCTGCCC TGGGGTCTCC GCAGTCCCCA       1140

TGGCCCCTTC CCTGTCTGGG TCCTGGGGGG GCGGGTGCAG GAACTACACG GCCAGCAGCA       1200

CATCCGCCCC TGCCCTGTGG CACCTGCTCC CCTGGCACAG GGCACAGGAG GGCCTTCCGA       1260

GAAGAGACCT TCTGTCCCCT CGCCCCTCCA CAGTCGGCAA GCCTGCACTG GGGTCCCCAG       1320

GGCAGGGGCC CAGGCTCTGC AGTCCGCTTC TCCTGTCCCC TCGCCCCTCC ACAGGTGGCA       1380

AGCAGCACAT TCTTGCTTAC AGAGTCCAGA AAACCACACA CACACACACA CACACACACA       1440

CACACACACA CACACAAAAA AAAACACTTG CCGACGAGAC AGCCCGCACT TGGTACCCGC       1500

CTCCCATGCT GCTTCTCCCG GCTCTGAGCC GTGGGTACAA CCCCTCGGGG GGGGGGGGG        1560

GAGGATTTCT CTCCCCCACC CCCAGTCTTC CTAGCAGATG TGCATCCCGG CCAACATGGA       1620

GGGAAATGGA CAACCTTGCC GGGGACTTTT TTTTCTTTCA TTTGAAACCA TGACCGCAGC       1680

CGTTCCTCCA ACCTGGCCTG ACCTCTCCAC GTGTCCAAGG AGGAAGCCCC CTGGCCCAGT       1740

TGAGGCCTCG CCAACCTGGC ACCCCTCCAG GCTCCTCCTC CTGCTCCAAC CTTTAAATGC       1800

ATCCCGGGGC CCCAGAACAC CATCCGACAC CTGCCTGCTG CCCACCACCA GCCTACCACC       1860

TGCCACC ATG CGC TGT CTC ATC AGC CTG GCC CTC GGC CTG CTC GCC CTG        1909
        Met Arg Cys Leu Ile Ser Leu Ala Leu Gly Leu Leu Ala Leu
         1               5                  10

GAG GCG GCC CTC GCT CTG GCC CCC AAA TTC ATC GCT CCA G                   1949
Glu Ala Ala Leu Ala Leu Ala Pro Lys Phe Ile Ala Pro
 15              20                  25

GTAGGCCCAG CTGCCTTCCT CACTCCGGGA CGCACTCAGG AGGGGTCCCC TTGTCTCATA       2009

TCTGCTCCAG AGTCCACCCA AGACTCGTGG CCTTGGTGGC TCCGTGACAG GGACACAGCC       2069

GGCCAGGAGA GGAGCAGAGG AGGCTCACCC TTGGGAGGGG GTCCTGGGTG GCAGGAAACC       2129

AGCGCCCTGT CCCCACGCAG GGGGCCACGA GCTGCCAGGC CAAGGACTGG TCACCTCCGG       2189

CCAGGACCTG ACTGGCCTGC TCCTGCAGTG GACCTGTGTC TTGTGTCCCC ACTTCCACAG       2249

CTGACTTCAC TCGCTTTTGT CAGCCGTATC GCAGTTCTGG CCACGGGTTT TGTTTTGTT        2309

TTGTTTTGTT TTGTTTTGTT TTGCCCTCCT TCCTGGGCTG CTGGGGGCCA GGCTCCCACG       2369

GTTCTGTCCT CGCCCTCCTC CAAGGAGCCC TGGGGGTGGG AGGGGCAGGG CTGCGGGCCC       2429

CCACACACTT GCTCGTCCTG CCCCGTGTGC AG  TG CAG GTC ATG TGC CCC GAG        2481
                                    Val Gln Val Met Cys Pro Glu
                                                    30

CCC AGC TCT TCC GAG GAG ACG CTC TGC CTC AGT GAC AAC GAC TGT CTC        2529
Pro Ser Ser Ser Glu Glu Thr Leu Cys Leu Ser Asp Asn Asp Cys Leu
 35              40                  45                  50

GGC AGC ACC GTG TGC TGT CCC AGC GCC GCC GGC GGC TCC TGC AGA ACC        2577
Gly Ser Thr Val Cys Cys Pro Ser Ala Ala Gly Gly Ser Cys Arg Thr
             55                  60                  65

CCC ATC ATC G GTAACGTAGC CACACTGCAG GCCTCTCCGG AAGCCCACAC              2627
```

```
Pro Ile Ile

ACCTGCCCCA TGGCGCAGTC TCTCTGGGCC CCATCCACCT GCCCCGAGGC CTCTGTGCCA      2687

CCCCACAGGT CCCTGAGGGC TCCAGGATGC CCCAGTGCTG CGGGAGGTCC TGCGGTGAGA      2747

CCAGCAAGAG GGAGGCCACA GAGACCCAGC TGACCTCAGG GGTCCCCCGG CGCTCAACTT      2807

GTCTCAGTGG GGTCTTGCGG GTCAGGTCTG GGGGGGCCCA TGTTACAGGG TGTGACCAGA      2867

AAAGGCCTGT CTCTCCCCAG  TC CCT ACC CCC AAG GCT GGC CGC TGC CCC          2916
                          Val Pro Thr Pro Lys Ala Gly Arg Cys Pro
                                   70              75

TGG GTG CAG GCG CCA ATG CTG TCC CAG TTG TGT GAG GAG CTG AGC GAC        2964
Trp Val Gln Ala Pro Met Leu Ser Gln Leu Cys Glu Glu Leu Ser Asp
 80              85                  90                  95

TGT GCC AAC GAC ATC GAG TGC AGG GGC GAC AAG AAG TGC TGC TTC AGC        3012
Cys Ala Asn Asp Ile Glu Cys Arg Gly Asp Lys Lys Cys Cys Phe Ser
                100                 105                 110

CGC TGC GCC ATG CGC TAT CTG GAA CCC ATC CTA G GTATGTGTCC               3056
Arg Cys Ala Met Arg Tyr Leu Glu Pro Ile Leu
            115                 120

TGAGCCCTCC CCAGGCAGGG CTGTCCCTTC AGCAGGGCCC AGGGCTCAGG AGTGGATGTG      3116

GGTGAGTGAA GGGCACTCGG GGACGCAGGT GGCAGGCGGG ACTTGGCCCT GGGTGGCTCA      3176

CAGGCCAGCC TGTACCTTTG CCACTGATCT GAGAGGGAGT GCAGCACAGC TCCAGGTATC      3236

GGAGGAGTCG AAGGTTAGGA GCCTGGGGTG TTGTCCACCA GCTGTGGCCT GCATATTCCT      3296

TCCTACAGAG GGGGGGGGGC AGAGGCGGGG AGGGGGCTCT GCTTGCGCAC TAGGGTCCCT      3356

GGCAGTGAAC CACAGCCGAC ACTGACCTCC CACCTTGTCC CCACCTGTGT CTCCTGCAGAG     3417
                                                                Glu

AGC ACT CCC CAG TGAGCCGCCT ACCCAGGAGT CCCTGGCTGC CAGGAGAGTT            3469
Ser Thr Pro Gln
        125

GGGCCTGAGT CCCCCTCTTG GACCCAGAGA GCTTGTGACG CGTCCTCCCT GCTGCTAATA      3529

AAACTACTCA GCTTCATGGC TCTGGTTGTC TGTCCATCTG CCCTGGGAGC TTGGGAAACC      3589

AGTGACCCCA AGTAGGCACA GCTCTGCCTG GCTCAGCAGC CCAGCACGAC GTCCGAGGGA      3649

ATGGACTAGA CCCCAAGATA ACGCTTACCT CCCTCCACCC CTGTTTGAGC TTGCCAGGAA      3709

GGGCAGCAGG CCATTCAGGG TGAGCCACGC CCTCAGGGAG CCCCCACGTA CCTGTGAGGT      3769

CACTTCCCTG GCTTCAGTG CCCACGAACC CCTGTCCTTT TCCGTGGCAG TCAGTGAACA       3829

GAGTAAGAAG AGGAGAGTGA GCTCCAGCCT GTGAAGTTCA GCCCTTCCTG GGTGTGGCAC      3889

AGAGACAGGC CAGGCTGTCC CAGGCTGTCC CAGGCTGCTG GCCGGGGGT GCACAGAGGC       3949

CTCGCAGAAG AAAGAGCCAT CATGTGCAGA GTGAGAGGAA AGGCCCCCCC AGACAGAGGC      4009

ATGTGCAGGA CGCCTCGGCC GGGACGTGGA TCGCCAGAGG CCCCTGCGCG CCATGCTGGG      4069

GTGAGGGGAC GTTAGGACA CAGGGCCTAA TGGAGAGCAG CTAGGTCATG GGGGTGCTGC       4129

CTCCTGAGAC TGGATTCGTC CCCTCGAG                                         4157

(2) INFORMATION FOR SEQ ID NO:3:

(i) SEQUENCE CHARACTERISTICS:
        (A) LENGTH: 127 amino acids
        (B) TYPE: amino acid
        (D) TOPOLOGY: linear (ii) MOLECULE TYPE: protein (xi) SEQUENCE DESCRIPTION: SEQ ID NO:3:
```

-continued

```
Met Arg Cys Leu Ile Ser Leu Ala Leu Gly Leu Leu Ala Leu Glu Ala
 1               5                  10                  15

Ala Leu Ala Leu Ala Pro Lys Phe Ile Ala Pro Val Gln Val Met Cys
                20                  25                  30

Pro Glu Pro Ser Ser Ser Glu Glu Thr Leu Cys Leu Ser Asp Asn Asp
            35                  40                  45

Cys Leu Gly Ser Thr Val Cys Cys Pro Ser Ala Ala Gly Gly Ser Cys
        50                  55                  60

Arg Thr Pro Ile Ile Val Pro Thr Pro Lys Ala Gly Arg Cys Pro Trp
 65                  70                  75                  80

Val Gln Ala Pro Met Leu Ser Gln Leu Cys Glu Glu Leu Ser Asp Cys
                85                  90                  95

Ala Asn Asp Ile Glu Cys Arg Gly Asp Lys Lys Cys Cys Phe Ser Arg
            100                 105                 110

Cys Ala Met Arg Tyr Leu Glu Pro Ile Leu Glu Ser Thr Pro Gln
            115                 120                 125
```